(12) United States Patent
Samain et al.

(10) Patent No.: US 6,703,028 B1
(45) Date of Patent: *Mar. 9, 2004

(54) COSMETIC COMPOSITION CONTAINING AN AQUEOUS POLYMER DISPERSION AND AN INSOLUBLE SILICONE, AND PROCESS AND USE THEREOF

(75) Inventors: Henri Samain, Bievres (FR); Daniel Bauer, Le Raincy (FR); Jean-Michel Sturla, St Cloud (FR)

(73) Assignee: L'Oreal, S.A. (FR)

( * ) Notice: Subject to any disclaimer, the term of this patent is extended or adjusted under 35 U.S.C. 154(b) by 269 days.

This patent is subject to a terminal disclaimer.

(21) Appl. No.: 09/689,818

(22) Filed: Oct. 13, 2000

Related U.S. Application Data

(63) Continuation of application No. 08/694,628, filed on Aug. 9, 1996, now Pat. No. 6,165,446.

(30) Foreign Application Priority Data

Aug. 11, 1995 (FR) .............................. 95 09773

(51) Int. Cl.$^7$ ............................ A61K 7/00; A61K 9/00; A61K 7/06
(52) U.S. Cl. ...................... 424/401; 424/47; 424/70.11; 514/844; 514/943
(58) Field of Search ................ 424/47, 70.11, 424/401; 514/844, 943

(56) References Cited

U.S. PATENT DOCUMENTS

| | | | |
|---|---|---|---|
| 4,085,264 A | | 4/1978 | Seib et al. |
| 4,798,721 A | * | 1/1989 | Yahagi et al. ................. 424/70 |
| 5,160,730 A | | 11/1992 | Dubief et al. |
| 5,306,484 A | | 4/1994 | Potthoff-Karl et al. |
| 5,458,871 A | | 10/1995 | Malawer et al. |
| 5,567,428 A | | 10/1996 | Hughes |
| 6,165,446 A | * | 12/2000 | Samain et al. ................. 424/47 |

FOREIGN PATENT DOCUMENTS

| | | | |
|---|---|---|---|
| DE | A-4314305 | 11/1994 | |
| EP | A-0288012 | 10/1988 | |
| EP | A-0320218 | 6/1989 | |
| EP | A-0323715 | 7/1989 | |
| EP | A-0379082 | 7/1990 | |
| EP | A-0424260 | 4/1991 | |
| EP | A-0590604 | 4/1994 | |
| FR | A-2351135 | 12/1977 | |
| FR | A-2697160 | 4/1994 | |
| WO | WO-A-9221316 | 12/1992 | |
| WO | 95/28908 | * 11/1995 | ............ A61K/7/06 |
| WO | WO-A-9528909 | 11/1995 | |

OTHER PUBLICATIONS

English language Derwent Abstract of FR–A–2697160.
English language Derwent Abstract of DE–A–4314305.
Chemical Abstracts, vol. 89, No. 14, p. 517, Abstract No. 117456m, Oct. 2, 1978, "Hair–Setting Preparations".

* cited by examiner

*Primary Examiner*—Shengjun Wang
(74) *Attorney, Agent, or Firm*—Finnegan, Henderson, Farabow, Garrett, & Dunner, L.L.P.

(57) ABSTRACT

An aqueous or aqueous/alcoholic cosmetic composition which can be sprayed, comprising an aqueous dispersion of insoluble film-forming polymer particles and at least one insoluble silicone, wherein the polymer particles are present in a concentration greater than 15%, relative to the total weight of the composition, and further wherein the glass transition temperature of the insoluble polymer particles ranges from 15 to 35° C.

The invention also relates to a process for the cosmetic treatment of keratinous substances using these compositions and to the use of the silicone for improving the quality of the spraying of the composition.

51 Claims, No Drawings

COSMETIC COMPOSITION CONTAINING AN AQUEOUS POLYMER DISPERSION AND AN INSOLUBLE SILICONE, AND PROCESS AND USE THEREOF

This application is continuation of U.S. application No. 08/694,628 Now U.S. Pat. No. 6,105,446, filed Aug. 9, 1996, which claim foreign priority of France 95 09773, filed Aug. 11, 1995.

The present invention relates to an aqueous or aqueous/alcoholic cosmetic composition containing an aqueous dispersion of insoluble film-forming polymer particles and an insoluble silicone, the polymer particles being present at a concentration greater than 15% by weight, relative to the total weight of the composition.

The invention also relates to a cosmetic treatment process using these compositions and to the use of an insoluble silicone for improving the quality of the spraying of a cosmetic composition containing an aqueous dispersion of insoluble film-forming polymer particles.

Hair compositions to be sprayed onto hair are essentially composed of a solution, most often aqueous/alcoholic, and of a polymer, optionally as a mixture with various cosmetic adjuvants. This solution is packaged either in a pump-action spray or in an appropriate aerosol container which is pressurized using a propellant gas.

For a number of years, very particular interest has been displayed in producing essentially aqueous cosmetic hair compositions. In fact, the use of alcohol, such as ethanol or isopropanol, alone or as a mixture with a small proportion of water, can exhibit certain disadvantages, in particular an increase in flammability when the composition is in the form of an aerosol lacquer.

More generally, a search is under way to reduce the use of compounds known as VOCs (Volatile Organic Compounds), which are volatile at atmospheric pressure, which are present in cosmetic compositions. The VOCs are mainly propellants and certain solvents, such as ethanol.

In order to decrease the amount of VOC, attempts have been made to replace solvents, such as ethanol, by water. However, while the majority of water-soluble film-forming polymers can, in solution in water, result in the production of hair fixing compositions, the latter exhibit major disadvantages.

Thus, the essentially aqueous compositions of these polymers do not make it possible to obtain high degrees of fixing. It has certainly been proposed to use these water-soluble polymers at high concentrations, but the increase in concentration causes such an increase in the viscosity of the compositions that it is only with great difficulty that satisfactory spraying can be obtained. Even if correct spraying is obtained, these aqueous compositions exhibit a particularly long drying time compared to alcoholic compositions and are therefore of little practical interest.

It has also been proposed to use aqueous dispersions of insoluble polymer particles instead of polymers dissolved in aqueous, alcoholic or aqueous/alcoholic compositions. However, to date, the results obtained are still not satisfactory.

In particular, the inventors have observed that, when attempts have been made to use high concentrations of polymer particles in aqueous dispersion, the spraying of the spray is not satisfactory. The sprayed liquid particles are not fine, the spray is often narrow, that is to say non-diffuse, and spraying is uneven. Moreover, the spraying orifice has a tendency to become blocked.

As the spraying is an essential component in the final quality of a composition to be sprayed onto hair, it is essential to overcome these disadvantages in order to obtain good distribution of the spray over the whole of the hair.

The inventors have now discovered that a cosmetic composition containing, in a cosmetically acceptable medium, an aqueous dispersion of insoluble polymer particles and an insoluble silicone, the polymer particles being present at a concentration greater than 15% by weight, relative to the total weight of the cosmetic composition, and the glass transition temperature of the insoluble polymer particles of the composition ranging from 15 to 35° C., makes it possible to overcome the disadvantages described above, that is to say the composition can be easily and correctly sprayed.

The compositions according to the invention make it possible to obtain good spraying; the spray is even and the sprayed drops are fine. The compositions are readily distributed over the whole of the hair. Moreover, surprisingly, the shape-retention power of the compositions is not decreased by the addition of a silicone. Finally, the drying times are low.

The subject of the present invention is therefore a cosmetic composition comprising, in a cosmetically acceptable aqueous or aqueous/alcoholic medium, an aqueous dispersion of insoluble polymer particles and an insoluble silicone, the polymer particles being present at a concentration greater than 15%, relative to the total weight of the cosmetic composition, and a glass transition temperature of the insoluble polymer particles of the composition ranging from 15 to 35° C.

Preferably, the insoluble silicone is present in an amount sufficient to obtain a fine, diffuse, and even spray.

The invention also relates to the use of an insoluble silicone (i.e. insoluble in an aqueous or aqueous/alcoholic medium) for improving the quality of the vaporization/spraying of a cosmetic composition containing, in a cosmetically acceptable aqueous or aqueous/alcoholic medium, an aqueous dispersion of insoluble polymer particles, the polymer particles being present at a concentration greater than 15%, relative to the total weight of the cosmetic composition and the glass transition temperature of the insoluble polymer particles of the composition ranging from 15 to 35° C.

The compositions according to the invention exhibit, in addition to the above-mentioned advantages, a good shape-retention power, a good resistance to moisture, good removal on shampooing and on brushing and a good rate of drying.

However, other characteristics, aspects or advantages of the invention will become more completely apparent on reading the detailed description which will follow, and the concrete but in no way limiting examples intended to illustrate it.

The aqueous dispersions of insoluble polymer particles which can be used according to the invention are generally obtained by suspension or emulsion polymerization or copolymerization of monomers according to processes which are well known in the state of the art (such dispersions are also known under the name of "latex").

The aqueous dispersions can result in particular from the polymerization or copolymerization of monomers such as styrene, butadiene, ethylene, propylene, vinyltoluene, vinyl propionate, vinyl alcohol, acrylonitrile, chloroprene, vinyl acetate, urethanes, isoprene, isobutene, vinyl ether, vinylpyrrolidone, vinylimidazole and acrylic or methacrylic, maleic, crotonic or itaconic acids, their esters or their amides.

According to the invention, it is possible, for example, to use an aqueous dispersion comprising an acrylic copolymer formed from:

(a) approximately 35 to 74% by weight of an alkyl acrylate;

(b) approximately 25 to 65% by weight of alkyl methacrylate; and (c) approximately 1 to 15% by weight of one or a number of ethylenic carboxylic acids having from 3 to 5 carbon atoms, wherein the alkyl radicals have from 1 to 5 carbon atoms and the percentages being expressed by weight are relative to the total weight of copolymer.

The alkyl acrylate is preferably chosen from methyl acrylate, ethyl acrylate, propyl acrylate and butyl acrylate. Ethyl acrylate is more particularly preferred.

The concentration of alkyl acrylate more preferably ranges from 40 to 70% by weight and even more preferably from 50 to 60% by weight, relative to the total weight of the copolymer.

The alkyl methacrylate is preferably chosen from methyl methacrylate, ethyl methacrylate, propyl methacrylate and butyl methacrylate. Methyl methacrylate is more particularly preferred.

The concentration of alkyl methacrylate more preferably ranges from 30 to 50% by weight, and even more preferably from 30 to 40% by weight, relative to the total weight of the copolymer.

The preferred ethylenic carboxylic acids are acrylic acid, methacrylic acid, crotonic acid, itaconic acid or their mixtures. Acrylic acid and methacrylic acid are more particularly preferred.

According to the invention, it is possible to use salts of these carboxylic acids.

The concentration of ethylenic carboxylic acids, or of their salts, more preferably ranges from 5 to 15% by weight, and even more preferably from 8 to 12% by weight, relative to the total weight of the copolymer.

In a particularly preferred embodiment of the invention, acrylic acid is used with methacrylic acid, each in a concentration ranging from 2 to 10% by weight, the total of these two acids not exceeding 15% by weight, relative to the total weight of the copolymer.

The copolymer can also contain small amounts, that is to say preferably less than 10%, and more preferably less than 5% and still more preferably less than 2%, of a polymerizable monomer other than those mentioned above.

Generally, the dispersion contains at least 0.5% of surfactant, making possible the dispersion and the maintenance in dispersion of the insoluble polymer. According to the invention, it is possible to use any type of surfactant but preferably a non-ionic surfactant and more preferably polyoxyalkylenated ($C_6$–$C_{12}$)alkylphenols.

The mean size of the particles of the copolymer in the dispersion preferably ranges from 0.1 to 1 micron.

According to a particularly preferred embodiment of the invention, use is made of a copolymer comprising from 50 to 60% by weight of ethyl acrylate, from 30 to 40% by weight of methyl acrylate, from 2 to 10% by weight of acrylic acid and from 2 to 10% by weight of methacrylic acid, the total concentration of acrylic and methacrylic acid not exceeding 15% by weight, relative to the total weight of the acrylic copolymer.

Such a copolymer is, for example, described in Patent Application EP-A-590604, the disclosure of which is specifically included herein by way of reference.

An aqueous dispersion of the acrylic copolymer described above comprising 25% by weight of an ethyl acrylate/methyl methacrylate/methacrylic acid/acrylic acid copolymer having a glass transition temperature of approximately 30° C. is sold in particular under the trade name Amerhold DR-25 by the company Amerchol.

Aqueous dispersions which are also particularly well suited to the invention are aqueous dispersions of styrene/butyl acrylate copolymers, such as, for example, the product sold under the trade name Uramul SC 70 by the company D.S.M. Resins.

The concentration by weight of the insoluble polymer particles in the compositions according to the invention preferably ranges from greater than 15% up to a concentration no greater than that at which the insoluble polymer particles can be maintained in an aqueous dispersion, and more preferably from greater than 15% to 35% by weight, relative to the total weight of the composition.

The insoluble silicones which can be used in the context of the present invention can be chosen from all those already known per se, namely, in particular, those described in Patent Applications EP-A-0,1 81,773 and EP-A-0,473,508, the disclosures of which are specifically incorporated herein.

It is, of course, possible to use mixtures of silicones. Insoluble silicone is understood to mean a silicone which is insoluble in the medium which is used as vehicle for the compositions according to the invention.

Thus, according to the present invention, it is possible to use any silicone known per se, whether a silicone oil, a silicone resin or alternatively a silicone gum. Silicones are organosilicon polymers or oligomers of variable molecular weight, with a linear or cyclic, branched or crosslinked structure, obtained by polymerization and/or polycondensation of suitably functionalized silanes and essentially composed of repeating main units in which the silicon atoms are connected to each other by oxygen atoms (siloxane bond), optionally substituted hydrocarbon radicals being directly bonded via a carbon atom on the said silicon atoms.

The most common hydrocarbon radicals are alkyl radicals, and in particular methyl radicals, fluoroalkyl radicals, aryl radicals, and in particular phenyl radicals, and alkenyl radicals, and in particular vinyl radicals; other types of radicals capable of being bonded either directly or via a hydrocarbon radical to the siloxane chain are in particular hydrogen, halogens, and in particular chlorine, bromine or fluorine, thiols, alkoxy radicals, polyoxyalkylene (or polyether) radicals, and in particular polyoxyethylene and/or polyoxypropylene radicals, hydroxyl or hydroxyalkyl radicals, substituted or unsubstituted amino groups, amide groups, acyloxy or acyloxyalkyl radicals, hydroxyalcylamino or aminoalkyl radicals, quaternary ammonium groups, amphoteric or betaine groups or anionic groups, such as carboxylate, thioglycolate, sulphosuccinate, thiosulphate, phosphate and sulphate groups. This list of so-called "organomodified" silicones is, of course, in no way limiting.

The silicones which can be used in the context of the present invention are generally those which are in particular described in "Encyclopedia of Chemical Technology, Kirk-Othmer, Third Edition, 1982, volume 20, pp. 922 et seq." and in "Chemistry and Technology of Silicones, Walter Noll, Academic Press Inc, San Diego, Calif., 1968", the disclosures of which are specifically incorporated herein. The average molecular weight of the silicones which can be used according to the invention can range from 100 to several millions, preferably from 1000 to 1,000,000.

According to the present invention, it is possible, of course, either to use one silicone or to use a number of different silicones.

Mention may in particular be made, as examples of silicones which can be used in the compositions according to the invention, of polydialkylsiloxanes, polyalkylarylsiloxanes, polydiaryldialkylsiloxanes and more generally still all the polyalkylarylsiloxanes described in the patent application published under the number WO 93/05762, the teaching of which is specifically incorporated by reference herein.

According to a particularly preferred embodiment of the present invention, the silicones used are chosen from polydiorganosiloxanes (oils, gums or resins), more preferably polydialkylsiloxanes or polyalkylarylsiloxanes and still more preferably polydimethylsiloxanes, which are optionally modified.

Silicone gums are particularly preferred and in particular those of polydialkylsiloxanes or of polyalkylarylsiloxanes, which are optionally modified. They can be used alone or as a mixture in a solvent chosen, for example, from volatile silicones, polydimethylsiloxane or polyphenylmethylsiloxane oils, isoparaffins, pentane, dodecane or their mixtures.

The silicone or silicones are present in the compositions in accordance with the invention in proportions generally ranging from 0.05 to 10% by weight, more preferably from 0.1 to 3% by weight, relative to the total weight of the composition.

The cosmetically acceptable aqueous or aqueous/alcoholic continuous medium which is used as vehicle for the compositions according to the invention is preferably composed of water or a mixture of water and of cosmetically acceptable solvents, such as monoalcohols, polyalcohols and glycol ethers, which can be used alone or as a mixture.

More preferentially still, the said vehicle is essentially composed of water.

The pH of the compositions according to the invention generally ranges from 2 to 9, and more preferably from 3 to 8. It can be adjusted to the desired value by means of basifying or acidifying agents commonly used in cosmetics for this type of application.

When the composition according to the invention is pressurized in the form of an aerosol, the aerosol comprises the composition described above, known as juice, and at least one propellant agent which can be chosen from volatile hydrocarbons, such as n-butane, propane, isobutane or pentane, chlorinated and/or fluorinated hydrocarbons and their mixtures.

It is also possible to use, as propellant agent, carbon dioxide gas, nitrous oxide, dimethyl ether, nitrogen, compressed air and their mixtures.

In such a system, the concentration of propellant(s) generally ranges from 10 to 50% by weight, relative to the total weight of the pressurized composition and more preferably from 15 to 35% by weight, relative to the total weight of the pressurized composition.

According to a preferred embodiment of the invention, the concentration of polymer particles is at least 10%, relative to the total weight of the pressurized composition (juice+propellant), more preferentially from at least 10% up to a concentration no greater than that at which the insoluble polymer particles can be maintained in an aqueous dispersion, and still more preferentially ranges from 10 to 35% by weight, relative to the total weight of the pressurized composition.

The invention also relates to the use of an insoluble silicone for improving the quality of the vaporization or of the spraying of cosmetic compositions pressurized as aerosols containing a cosmetic composition described above and at least one propellant agent, the polymer particles being present at a concentration of at least 10%, relative to the total weight of the pressurized composition and the glass transition temperature of the insoluble polymer particles of the composition ranging from 15 to 35° C.

The compositions according to the invention (in the pressurized or unpressurized state) can additionally contain adjuvants, such as, surface-active agents, preserving agents, sequestrants, softeners, fragrances, dyes, viscosity-modifying agents, foam-modifying agents, antifoaming agents, pearlescence agents, moisturizing agents, antidandruff agents, antiseborrhoeic agents, sunscreening agents, proteins, vitamins, plasticizers, hydroxy acids or electrolytes.

The compositions according to the invention (in the pressurized or unpressurized state) can also contain conditioning agents. The latter may then be chosen from natural or synthetic oils and waxes, fatty alcohols, esters of polyhydric alcohols, glycerides, polymers or the mixtures of these various compounds.

The person skilled in the art will know how to choose the optional compound or compounds to be added to the composition according to the invention so that the advantageous properties intrinsically attached to the composition according to the invention are not, or not substantially, detrimentally affected by the envisaged addition.

The compositions according to the invention are, for example, rinsed or non-rinsed hair compositions. The compositions according to the invention are more particularly hair-setting lotions, lotions for blow drying, fixing compositions (lacquers) and styling compositions. The lotions are packaged in various forms, in particular in atomizers or pump-action sprays or in aerosol containers, in order to ensure application of the composition in the vaporized form.

A further subject of the invention is a process for the cosmetic treatment of keratinous substances, such as hair, characterized in that it involves applying to keratinous substances, in particular by spraying or vaporization, a cosmetic composition as defined above and then optionally rinsing with water, after an optional setting time.

An example illustrating the present invention will now be given without, however, limiting it in any way.

EXAMPLE

A composition (A) according to the invention was prepared and was compared with a composition (B) not in accordance with the invention. The two compositions were pressurized as aerosols.

A panel of 5 experienced testers evaluated the appearance of the spray obtained.

The grading ranged from 0 (bad: uneven spraying with large drops) to 5 (excellent: even spraying with fine drops).

The results are collated in the table below (AM means active material):

| In g AM | A (Invention) | B (Comparative) |
| --- | --- | --- |
| Amerhold DR 25[1] | 18 | 18 |
| Fluid DC 200[2] | 1 | — |
| Water, q.s. for | 100 | 100 |
| Appearance of the spray | 4.5 | 3 |

[1]Amerhold DR 25 from Amerchol: ethyl acrylate/methyl methacrylate/methacrylic acid/acrylic acid copolymer having a glass transition temperature of approximately 30° C. as an aqueous dispersion comprising 25% by weight of the copolymer.
[2]Fluid DC 200 from Dow Corning: polydimethylsiloxane The pressurization scheme was as follows:

| | |
|---|---|
| dimethyl ether (propellant) | 35 g |
| composition above (juice) | 65 g |

The spraying of the composition (A) was markedly finer and more even than that of the composition (B). The fixing power was, for its part, also good for both the compositions.

We claim:

1. A cosmetic composition comprising an aqueous dispersion of insoluble polymer particles and at least one insoluble silicone, wherein said insoluble polymer particles are present in a concentration greater than 15%, relative to the total weight of said cosmetic composition, wherein the glass transition temperature of said insoluble polymer particles ranges from 15 to 35° C., and wherein said aqueous dispersion comprises polymer particles instead of polymers dissolved in a solvent.

2. A cosmetic composition according to claim 1, wherein said insoluble polymer particles are present in a concentration ranging from greater than 15 to 35% by weight, relative to the total weight of said cosmetic composition.

3. A cosmetic composition according to claim 1, wherein said aqueous dispersion comprises at least one polymer/copolymer selected from polymerized and copolymerized monomers of styrene, butadiene, ethylene, propylene, vinyitoluene, vinyl propionate, vinyl alcohol, acrylonitrile, chloroprene, vinyl acetate, urethanes, isoprene, isobutene, vinyl ether, vinylpyrrolidone, vinylimidazole, acrylic acid, methacrylic acid, maleic acid, crotonic acid, itaconic acid, esters of acrylic acid, methacrylic acid, maleic acid, crotonic acid, and itaconic acid, and amides of acrylic acid, methacrylic acid, maleic acid, crotonic acid, and itaconic acid.

4. A cosmetic composition according to claim 1, wherein said insoluble polymer particles comprise at least one copolymer comprising:
   (a) approximately 35 to 74% of alkyl acrylate by weight, relative to the total weight of the copolymer;
   (b) approximately 25 to 65% of alkyl methacrylate by weight, relative to the total weight of the copolymer; and
   (c) approximately 1 to 15% of at least one ethylenic carboxylic acid or salt thereof having from 3 to 5 carbon atoms, by weight, relative to the total weight of the copolymer, wherein the alkyl radicals have from 1 to 5 carbon atoms.

5. A cosmetic composition according to claim 4, wherein said alkyl acrylate is selected from methyl acrylate, ethyl acrylate, propyl acrylate, and butyl acrylate.

6. A cosmetic composition according to claim 5, wherein said alkyl acrylate is ethyl acrylate.

7. A cosmetic composition according to claim 4, wherein said alkyl methacrylate is selected from methyl methacrylate, ethyl methacrylate, propyl methacrylate, and butyl methacrylate.

8. A cosmetic composition according to claim 7, wherein said alkyl methacrylate is methyl methacrylate.

9. A cosmetic composition according to claim 4, wherein the concentration of said alkyl methacrylate ranges from 30 to 50% by weight, relative to the total weight of the copolymer.

10. A cosmetic composition according to claim 9 wherein the concentration of said alkyl methacrylate ranges from 30 to 40% by weight, relative to the total weight of the copolymer.

11. A cosmetic composition according to claim 4, wherein said at least one ethylenic carboxylic acid or salt thereof is selected from acrylic acid, methacrylic acid, crotonic acid, itaconic acid, and salts thereof.

12. A cosmetic composition according to claim 11, wherein said at least one ethylenic carboxylic acid or salt thereof is selected from acrylic acid and methacrylic acid and salts thereof.

13. A cosmetic composition according to claim 4, wherein the concentration of said at least one ethylenic carboxylic acid or salt thereof ranges from 5 to 15% by weight, relative to the total weight of the copolymer.

14. A cosmetic composition according to claim 13, wherein the concentration of said at least one ethylenic carboxylic acid or salt thereof ranges from 8 to 12% by weight, relative to the total weight of the copolymer.

15. A cosmetic composition according to claim 12, wherein said at least one ethylenic carboxylic acid is a mixture of acrylic acid and methacrylic acid, wherein said acrylic acid is present in a concentration ranging from 2 to 10%, and said methacrylic acid is present in a concentration ranging from 2 to 10%, and further wherein the total concentration of said acrylic acid and said methacrylic acid does not exceed 15% by weight, relative to the total weight of the copolymer.

16. A cosmetic composition according to claim 3, wherein said cosmetic composition further comprises a second polymerized monomer different from said polymerized and copolymerized monomers and present in a concentration not greater than 10% relative to the total weight of said copolymer.

17. A cosmetic composition according to claim 3, wherein said cosmetic composition further comprises a second polymerized monomer different from said polymerized and copolymerized monomers and present in a concentration not greater than 5% relative to the total weight of said copolymer.

18. A cosmetic composition according to claim 3, wherein said cosmetic composition further comprises a second polymerized monomer different from said polymerized and copolymerized monomers and present in a concentration not greater than 2% relative to the total weight of said copolymer.

19. A cosmetic composition according to claim 1, wherein said cosmetic composition further comprises at least one surfactant present in a concentration sufficient to maintain the dispersion of the insoluble polymer.

20. A cosmetic composition according to claim 19, wherein said at least one surfactant is present in a concentration of at least 0.5% relative to the total weight of said cosmetic composition.

21. A cosmetic composition according to claim 19, wherein said at least one surfactant is a non-ionic surfactant.

22. A cosmetic composition according to claim 21, wherein said at least one non-ionic surfactant is selected from polyoxyalkylenated ($C_6$–$C_{12}$) alkylphenols.

23. A cosmetic composition according to claim 1, wherein the mean size of said insoluble polymer particles ranges from 0.1 to 1 micron.

24. A cosmetic composition according to claim 1, wherein said insoluble polymer particles comprise at least one ethyl acrylate/methyl acrylate/methacrylic acid/acrylic acid copolymer.

25. A cosmetic composition according to claim 24, wherein said copolymer comprises from 50 to 60% by weight of ethyl acrylate, from 30 to 40% by weight of methyl acrylate, from 2 to 10% by weight of acrylic acid and from 2 to 10% by weight of methacrylic acid, and wherein the total concentration of acrylic and methacrylic acid does not exceed 15% of the total weight of said copolymer.

26. A cosmetic composition according to claim 1, wherein said at least one insoluble silicone is present in a concentration ranging from 0.05 to 10%, by weight, relative to the total weight of the composition.

27. A cosmetic composition according to claim 26, wherein said at least one insoluble silicone is present in a concentration ranging from 0.1 to 3%, by weight, relative to the total weight of the composition.

28. A cosmetic composition according to claim 1, wherein said at least one insoluble silicone is selected from silicone oil, silicone gum and silicone resin.

29. A cosmetic composition according to claim 28, wherein said at least one insoluble silicone is selected from modified and unmodified polydialkylsiloxanes and modified and unmodified polyalkylarylsiloxanes.

30. A cosmetic composition according to claim 29, wherein said polydialkylsiloxanes are polydimethylsiloxanes.

31. A cosmetic composition according to claim 1, wherein the pH of said cosmetic composition ranges from 2 to 9.

32. A cosmetic composition according to claim 31, wherein the pH of said cosmetic composition ranges from 3 to 8.

33. A cosmetic composition according to claim 1, wherein said cosmetic composition in the span of is a hair-setting lotion, a lotion for blow drying, a fixing composition, or a styling composition.

34. A pressurized aerosol composition comprising an aqueous dispersion of insoluble polymer particles, at least one insoluble silicone, and at least one propellant agent, wherein said insoluble polymer particles are present in a concentration of at least 10%, relative to the total weight of said pressurized composition, and the glass transition temperature of said insoluble polymer particles ranges from 15 to 35° C.

35. A pressurized aerosol composition according to claim 34, wherein said at least one propellant agent is selected from volatile hydrocarbon, carbon dioxide gas, nitrous oxide dimethyl ether nitrogen, and compressed air.

36. A pressurized aerosol composition according to claim 35, wherein said volatile hydrocarbon is selected from n-butane, propane, isobutane pentane, chlorinated hydrocarbons, and fluorinated hydrocarbons.

37. A pressurized aerosol composition according to claim 34, wherein said insoluble polymer particles in said pressurized aerosol composition are present in a concentration ranging from 10 to 35%, relative to the total weight of the pressurized composition.

38. A pressurized aerosol composition according to claim 34, wherein said at least one propellant agent is present in a concentration ranging from 10 to 50% by weight, relative to the total weight of the pressurized composition.

39. A pressurized aerosol composition according to claim 38, wherein said at least one propellant agent is present in a concentration ranging from 15 to 35% by weight, relative to the total weight of the pressurized composition.

40. A cosmetic composition according to claim 1, wherein said cosmetic composition further comprises at least one adjuvant.

41. A pressurized aerosol composition according to claim 34, wherein said pressurized aerosol composition further comprises at least one adjuvant.

42. A cosmetic composition according to claim 1, wherein said cosmetic composition further comprises at least one conditioning agent selected from natural oils, natural waxes, synthetic oils, synthetic waxes, fatty alcohols, esters of polyhydric alcohols, glycerides, and polymers.

43. A process for treating a keratinous substance comprising the step of applying a cosmetically effective amount of a cosmetic composition according to claim 1 to said keratinous substance.

44. A process according to claim 43, wherein said keratinous substance is hair and wherein said step of applying said cosmetic composition to said keratinous substance is by spraying or vaporization.

45. A process according to claim 44, wherein said step of applying said cosmetic composition to said keratinous substance is followed by a step of rinsing said keratinous substance with water.

46. A process according to claim 45, wherein said step of rinsing said keratinous substance with water is performed after a setting time.

47. A method of obtaining a diffuse spraying of a cosmetic composition comprising the step of including at least one insoluble silicone in an aqueous dispersion of insoluble polymer particles, wherein said polymer particles are present in a concentration greater than 15%, relative to the total weight of the composition, have a glass transition temperature ranging from 15 to 35° C., wherein said aqueous dispersion comprises polymer particles instead of polymers dissolved in a solvent, and further wherein the concentration of said at least one insoluble silicone is sufficient to render said composition a diffuse spray.

48. A method of obtaining a diffuse spraying of a pressurized aerosol composition comprising the step of including at least one insoluble silicone in an aqueous dispersion of insoluble polymer particles, wherein said polymer particles are present in a concentration of at least 10%, relative to the total weight of the composition, and have a glass transition temperature ranging from 15 to 35° C., wherein said aqueous dispersion comprises polymer particles instead of polymers dissolved in a solvent, and further wherein the concentration of said at least one insoluble silicone is sufficient to render said composition a diffuse spray.

49. A cosmetic composition according to claim 1, wherein said at least one insoluble silicone is present in a concentration sufficient to obtain a diffuse spray.

50. A pressurized aerosol composition according to claim 34, wherein said at least one insoluble silicone is present in a concentration sufficient to obtain a diffuse spray.

51. A cosmetic composition according to claim 1, wherein said aqueous dispersion comprises an aqueous/alcoholic medium.

* * * * *

UNITED STATES PATENT AND TRADEMARK OFFICE
CERTIFICATE OF CORRECTION

PATENT NO. : 6,703,028 B1
DATED : March 9, 2004
INVENTOR(S) : Henri Samain et al.

It is certified that error appears in the above-identified patent and that said Letters Patent is hereby corrected as shown below:

<u>Column 7,</u>
Line 29, "vinyitoluene," should read -- vinyltoluene, --;

<u>Column 9,</u>
Line 28, "in the span of is" should read -- is in the form of --; and
Lines 41-42, "nitrous oxide dimethyl ether nitrogen," should read -- nitrous oxide, dimethyl ether, nitrogen, --.

Signed and Sealed this

Twenty-second Day of June, 2004

JON W. DUDAS
*Acting Director of the United States Patent and Trademark Office*